United States Patent
Levatter (10) Patent No.: US 7,125,404 B2
(45) Date of Patent: Oct. 24, 2006

(54) FIBER OPTIC LASER CATHETER AND METHOD OF USING IT

(76) Inventor: Jeffrey I. Levatter, 6865 Flanders Dr., Suite G, San Diego, CA (US) 92121

( * ) Notice: Subject to any disclaimer, the term of this patent is extended or adjusted under 35 U.S.C. 154(b) by 0 days.

(21) Appl. No.: 10/406,140

(22) Filed: Apr. 2, 2003

(65) Prior Publication Data

US 2004/0092915 A1    May 13, 2004

Related U.S. Application Data

(63) Continuation of application No. 09/784,294, filed on Feb. 14, 2001, now abandoned, which is a continuation of application No. 09/168,328, filed on Sep. 30, 1998, now abandoned, which is a continuation of application No. 07/966,582, filed on Oct. 26, 1992, now abandoned, which is a continuation of application No. 07/563,535, filed on Aug. 6, 1990, now abandoned.

(51) Int. Cl.
*A61B 18/18* (2006.01)

(52) U.S. Cl. ............................................. 606/7; 606/15

(58) Field of Classification Search ................... 606/7, 606/13–15
See application file for complete search history.

(56) References Cited

U.S. PATENT DOCUMENTS

| | | | |
|---|---|---|---|
| 3,538,919 A | 11/1970 | Meyer | |
| 4,418,688 A | 12/1983 | Loeb | |
| 4,461,283 A | 7/1984 | Doi | |
| 4,648,892 A | * 3/1987 | Kittrell et al. | ............... 65/387 |
| 4,718,417 A | 1/1988 | Kittrell et al. | |
| 4,770,653 A | * 9/1988 | Shturman | ..................... 606/7 |
| 4,781,681 A | 11/1988 | Sharrow et al. | |
| 4,784,132 A | 11/1988 | Fox et al. | |
| 4,793,359 A | 12/1988 | Sharrow | |
| 4,800,876 A | 1/1989 | Fox et al. | |
| 4,832,023 A | 5/1989 | Murphy-Chutorian et al. | |
| 4,844,062 A | 7/1989 | Wells | |
| 4,846,171 A | 7/1989 | Kauphusman et al. | |
| 4,848,336 A | 7/1989 | Fox et al. | |
| 4,850,351 A | 7/1989 | Herman et al. | |
| 4,862,886 A | 9/1989 | Clarke et al. | |
| 4,887,605 A | 12/1989 | Angelsen et al. | |
| 5,188,632 A | 2/1993 | Goldenberg | |
| 5,188,634 A | 2/1993 | Hussein et al. | |
| 5,217,454 A | 6/1993 | Khoury | |
| 5,331,069 A | 7/1994 | Bobsein et al. | |

(Continued)

FOREIGN PATENT DOCUMENTS

CA        2003069        5/1990

(Continued)

*Primary Examiner*—Michael Peffley
(74) *Attorney, Agent, or Firm*—Knobbe Martens Olson & Bear LLP (57) ABSTRACT

A fiber optic laser catheter assembly for use in removing, or largely debulking, obstructions or occlusions from a lumen in a living body. The catheter assembly includes an outer tubular sheath, an optical fiber extending through the sheath, and a fiber guide for holding the fiber within the sheath. In all of the disclosed embodiments, the obstructions are removed by controllably positioning an optical fiber's distal tip in a succession of selected radial and circumferential positions so as to sculpt away the obstruction without substantial risk of mechanically or thermally damaging the vessel. Several of the embodiments are configured such that the portion of the occlusion that can be reliably sculpted away has a radius greater even than the radius of the catheter assembly itself.

5 Claims, 13 Drawing Sheets

U.S. PATENT DOCUMENTS 5,437,659 A     8/1995   Leckrone
5,549,601 A * 8/1996   McIntyre et al. .............. 606/15
5,916,210 A * 6/1999   Winston ........................ 606/7

FOREIGN PATENT DOCUMENTS

| CA | 1295374 | 2/1992 |
| JP | A-1-148278 | 0/1989 |
| JP | U-1-172846 | 0/1989 |
| JP | U-62-92807 | 0/1987 |

* cited by examiner

FIBER OPTIC LASER CATHETER AND METHOD OF USING IT

RELATED APPLICATIONS

This application is a continuation of prior U.S. patent application Ser. No. of 09/784,294 filed Feb. 14, 2001, now abandoned which is a continuation of prior U.S. patent application Ser. No. of 09/168,328 filed Sep. 30, 1998, now abandoned which is a continuation of Ser. No. 07/966,582 filed Oct. 26, 1992, now abandoned which is a continuation of prior U.S. patent application Ser. No. 07/563,535 filed Aug. 6, 1990 now abandoned.

BACKGROUND OF THE INVENTION

This invention relates generally to fiber optic laser catheters and, more particularly, to catheters of this kind that are adapted to selectively position the optical fiber's distal tip to facilitate the sculpting out and debulking of an obstruction or occlusion in a vessel or lumen of a living body.

Catheters of this type are particularly useful in removing obstructions or occlusions such as those associated with arteriosclerosis lesions. In such procedures, the catheter is inserted into the diseased blood vessel and moved through the vessel to a position where its distal end lies immediately adjacent to the occlusion to be removed. A laser beam, commonly generated by a pulsed excimer laser, is then directed through the fiber and emitted from its distal tip, to ablate or otherwise remove the lesion. In this particular application, the laser catheter is being used to perform angiosurgery, a procedure that is commonly referred to as laser angioplasty.

In order to produce a successful angiosurgery outcome, a sufficiently larger laser-generated lumen must be created, without inflicting any damage on the remaining tissues. Blood vessels normally range in diameter from 1–10 millimeters. Therefore, any successful laser angiosurgery must be capable of producing a relatively large lumen that is typically 70–80% of the diameter of the native healthy vessel. In order to produce a sufficiently large lumen, the fiber optic laser light guide either must have a very large light-emitting area, nearly the size of the vessel, or must use a small diameter fiber and manipulate its distal tip to various positions within the vessel so as to sculpt out a large area. The large area fiber approach makes the catheter less flexible and its use therefore may be limited to non-tortuous vessels. The large area fiber approach also has the disadvantage of requiring a large catheter introducer sheath. The small fiber approach allows the catheter to have superior flexibility, but requires a method of fiber tip position control to create a lumen larger than the fiber diameter.

In the past, catheters of the large area type have been positioned using a guide wire that extends along the vessel and through the lumen of a stenosis or partial occlusion. This has not always proven to be a satisfactory means of positioning, however, because the hole in the occlusion is not always centrally located within the vessel. Moreover, in the case of a total occlusion, the hole is entirely absent and the use of a guide wire is not possible.

Catheters of the small diameter type include various kinds of structures for controlling either the X-Y or the radial and circumferential positions of the optical fiber's distal tip. This requires both a precise positioning of the catheter relative to the vessel and a precise positioning of the fiber tip within the catheter.

Even when the catheter can be precisely positioned within the vessel, it has generally proven to be difficult to sculpt away a sufficient amount of the occlusion without at the same time mechanically or thermally damaging the vessel. Such damage can occur by the mere physical rubbing of the catheter on the vessel lining, injuring the endothelial cells, or by excessive heating of various parts of the vessel wall by the laser beam. Such physical or thermal damage can lead to a significant rate of restinosis, in which hyperplasia, the excessive growth of smooth muscle cells, within the vessel is triggered, leading in some cases to even more severe blockages than were provided by the original occlusion being removed.

It should therefore be appreciated that there is a need for a fiber optic laser catheter that can be used to more reliably and more thoroughly remove an obstruction or occlusion in a vessel of a living body, in such a fashion so as not to inflict any further injury to the vessel. The present invention fulfills this need.

SUMMARY OF THE INVENTION

The present invention is embodied in a small diameter fiber optic laser catheter apparatus, and related method for using it, that is adapted to cooperate with a laser in substantially removing obstructions or occlusions from a vessel of a living body, with reduced risk of mechanically or thermally injuring the vessel. The apparatus includes a tubular catheter sheath sized to be received within the vessel, with a distal end of the catheter sheath being located proximal to the occlusion, and positioning means for engaging the vessel wall and positioning the catheter sheath at a selected radial position, e.g., centrally, within the vessel. An optical fiber extends through the sheath and includes a proximal end attachable to the laser and a distal end located immediately adjacent to the occlusion to be removed. In accordance with the invention, the apparatus further includes fiber guide means located within the catheter sheath and adapted to support the small diameter optical fiber's distal end. The small diameter fiber may be a single fiber or may be a bundle of smaller fibers. The fiber guide means is rotatable within the sheath, about the sheath's longitudinal axis, and it is configured to allow the fiber's distal tip to be positioned at any selected radial and circumferential location relative to the sheath. Since the only relative mechanical motion during use of the catheter apparatus is within the fiber guide means or between the fiber guide means and the sheath, the vessel is isolated from that motion, whereby the risk of damage to the vessel is substantially reduced. In addition, since the catheter apparatus is itself precisely positioned relative to the vessel, the risk of vessel perforation during operation of the laser, likewise, is substantially reduced.

During use of the catheter apparatus, the fiber guide means is typically continuously rotated at a low rate (e.g., less than 1000 rpm) while the laser is energized and the laser beam removes successive bits of tissue along a circumferential path. The use of a pulsed excimer laser, or other pulsed laser with a wavelength that is very highly absorbed in tissue, is quire advantageous in this application. With this type of laser, tissue is discretely removed only at or very near the fiber's distal tip and results in the generation of a very smooth surface lumen. The fiber guide means' rotation rate and the laser's pulse repetition rate are approximately adjusted so that successive laser pulses do not spatially overlap on the beam's circumferential path. This reduces any thermal build-up and minimizes damage in the surrounding tissues.

The fiber guide means can have any of several alternative preferred configurations. In one preferred embodiment, the fiber guide means includes a body and means defining a channel within the body sized to receive the optical fiber's distal end, with the channel having an axis skewed relative to the outer sheath's axis. The optical fiber is selectively movable axially within the channel such that the fiber's distal tip moves radially relative to the fiber guide means and the sheath. Selecting the distal tip's radial position facilitates the sculpting away of large diameter obstructions. Extending the optical fiber axially toward the lesion can even provide a positioning of the fiber's distal tip radially outside the sheath.

In an alternative embodiment, the fiber guide means includes a body and means defining a slot within the body sized to receive the optical fiber's distal end and to permit that distal end to be moved laterally within the slot, along an axis aligned substantially radially relative to the sheath. In this embodiment, the fiber guide means further includes biasing means for moving the fiber's distal end to a selected radial location within the slot. This biasing means can include an inflatable bladder and means for inflating the bladder such that it enlarges in size and forcibly urges the fiber's distal end radially within the slot.

In another embodiment, the fiber guide means includes spring bias means for yieldably urging the optical fiber's distal end radially relative to the sheath by an amount that varies as the optical fiber is moved axially relative to the sheath. In this embodiment, the fiber guide means further includes a body having a central passageway that terminates in a flared opening, and an elongated carrier for carrying the optical fiber's distal end. The carrier is sized to be received in the body passageway and to be axially and rotatable movable within the passageway. The spring bias means is located on the exterior of the elongated carrier and is adapted to engage the flared opening and thereby move the optical fiber's distal end radially relative to the sheath by an amount that varies in accordance with the fiber's axial position.

In yet another embodiment, the fiber guide means includes a body having a plurality of channels formed within it, each channel sized to receive the optical fiber and to hold its distal tip at a unique radial position. In use, the fiber is placed sequentially from one such channel to the next, with the fiber guide means being rotated relative to the sheath during each such placement, so as to sculpt out a series of concentric rings from the lesion.

In yet another embodiment, the fiber guide means includes a set of optical fiber holders, each having a separate channel formed in it for receiving the optical fiber's distal end. Each holder positions the fiber's distal tip at a unique radial position. In use, the separate holders are used sequentially, each sculpting out of the lesion a ring-shaped segment of unique radius.

Other features and advantages of the present invention should become apparent from the following description of the preferred embodiments, taken in conjunction with the accompanying drawings, which illustrate, by way of example, the principles of the invention.

DESCRIPTION OF THE PREFERRED EMBODIMENTS

Figure 1:
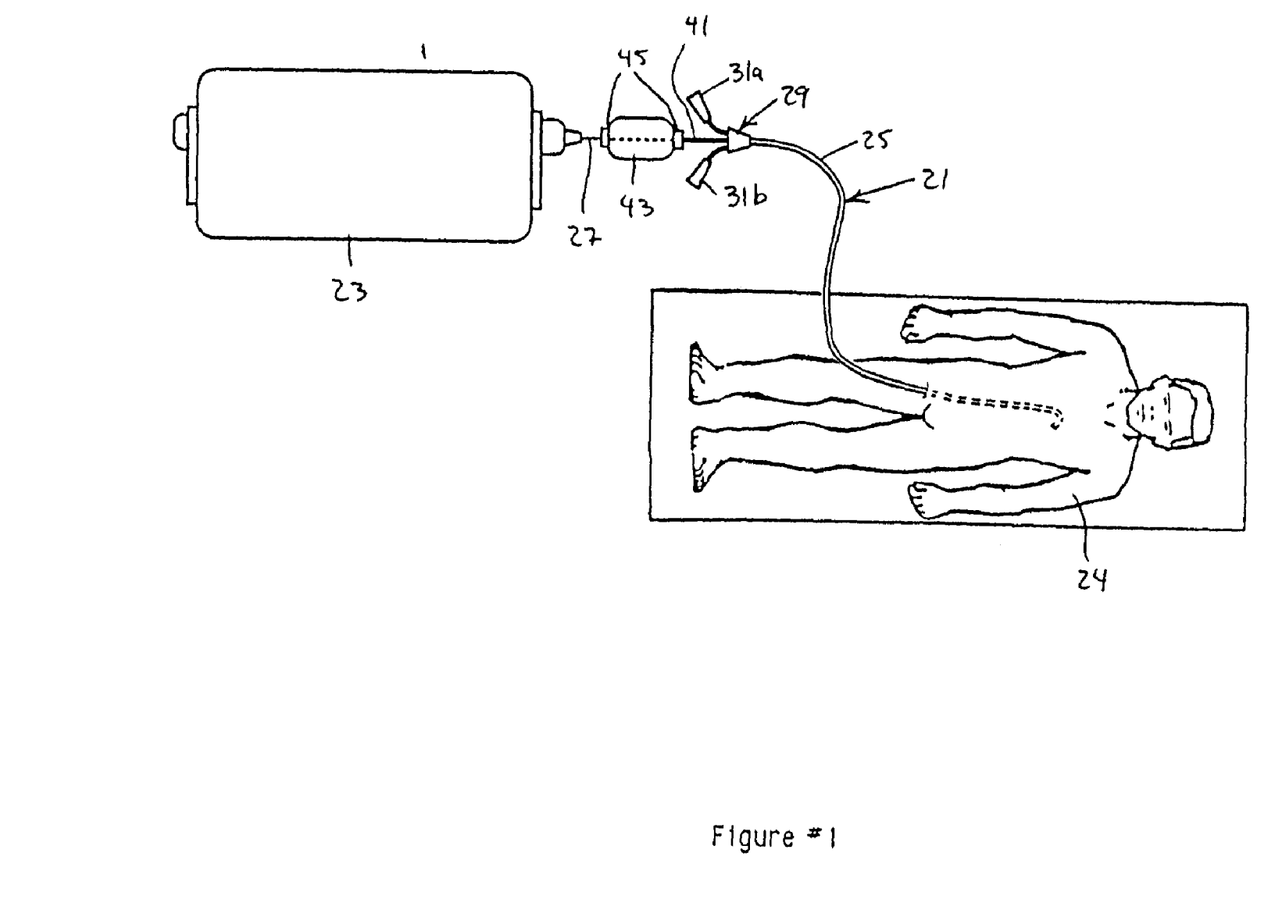
FIG. 1 is an illustration of a fiber optic catheter assembly constructed in accordance with the invention, for use in removing obstructions or occlusions from a vessel of a living body, the assembly being shown connected to a laser and a fiber guide rotation device.

With reference now to the drawings, and particularly to FIG. 1, there is shown, a fiber optic laser catheter assembly 21 adapted for use with a laser 23 in sculpting away a partial obstruction or total occlusion in a vessel of a patient 24. The catheter assembly is particularly useful with an excimer laser in removing arterial occlusions resulting from arteriosclerosis. The assembly includes an elongated, tubular sheath 25 sized to be insertable freely into the vessel, with an optical fiber 27 extending fully through the sheath. The fiber's proximal end is connected to the laser, and the fiber's distal end is located at or near the sheath's distal end. As is conventional, the assembly's proximal end includes an input device 29 having various fittings adapted for connection through fluid connection parts 31a and 31b to supplies for various solutions, etc.

Figure 2:
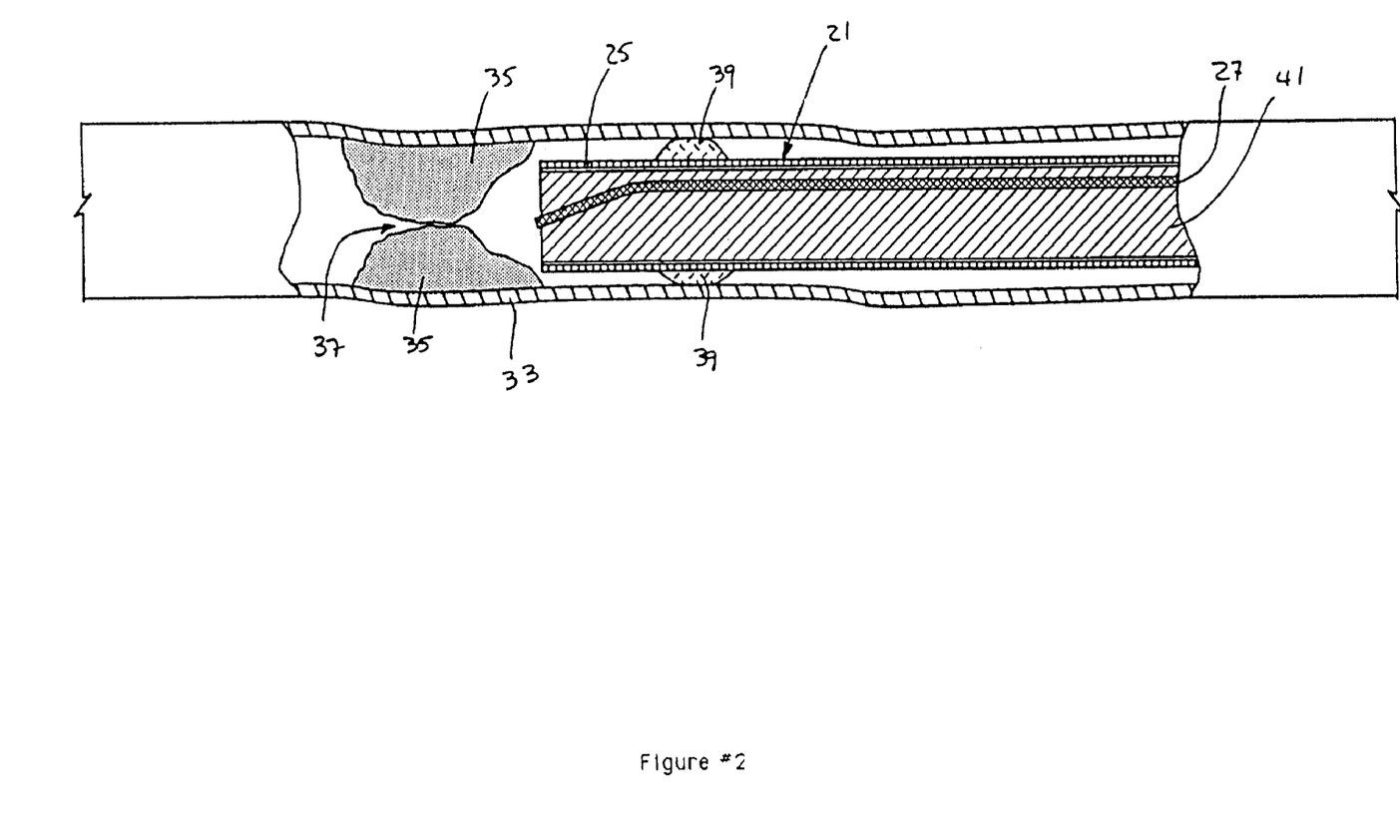
FIG. 2 is a side cross-sectional view of the distal end of a first embodiment of a catheter assembly in accordance with the invention, depicted within a vessel in a position to sculpt away part of an occlusion.
Figure 3:
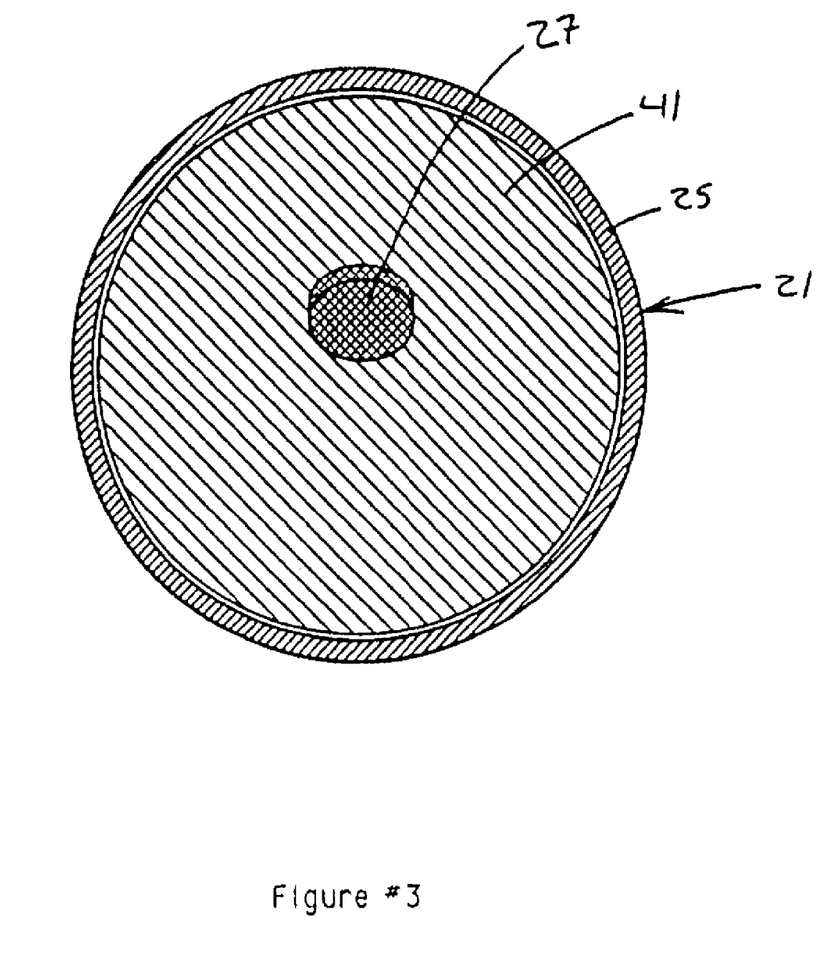
FIG. 3 is an end view of the catheter assembly of FIG. 2.
Figure 4:
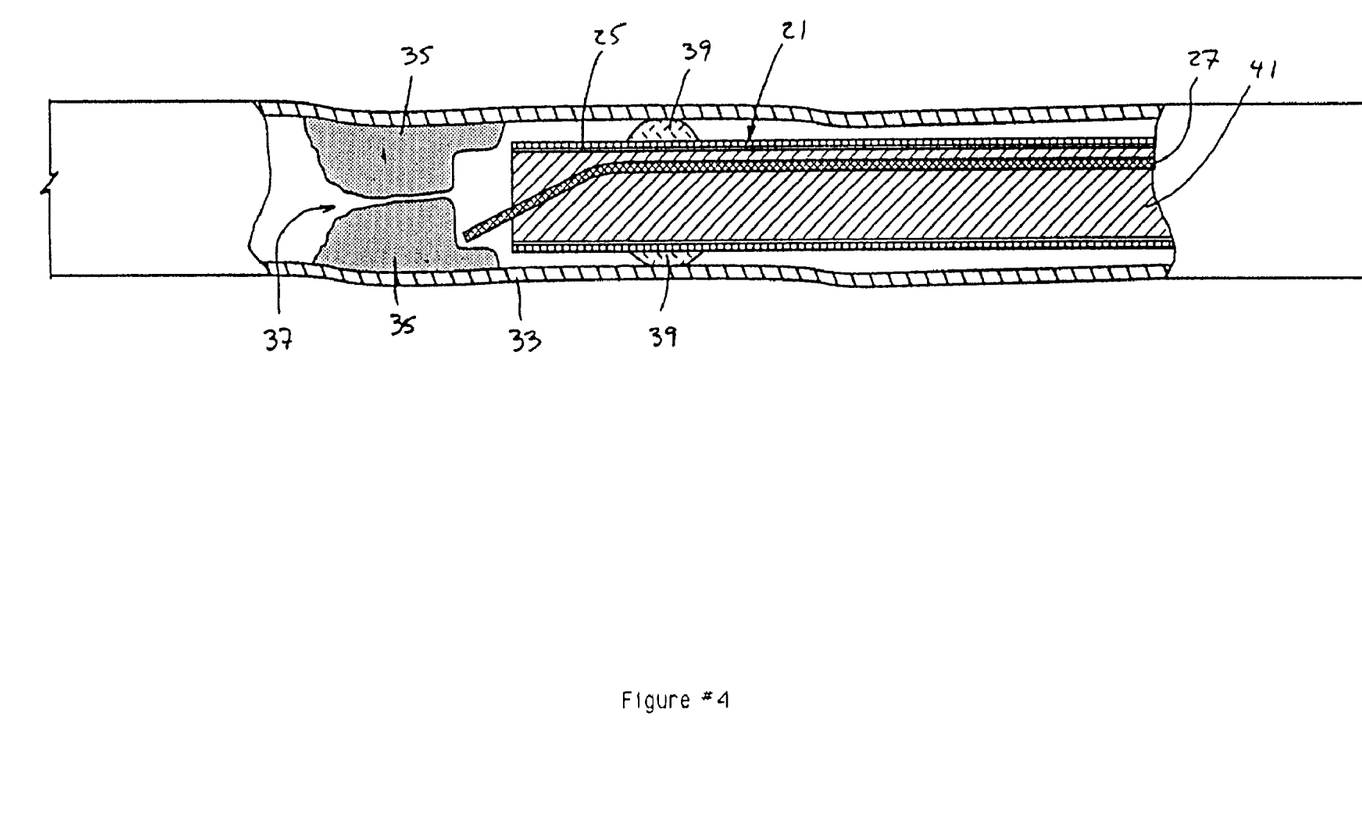
FIG. 4 is a side, cross-sectional view of the distal end portion of the catheter assembly of FIG. 2, but showing the optical fiber axially extended from a fiber guide contained in the assembly.

As shown in FIG. 2, a first embodiment of a fiber optic catheter assembly 21 is positioned within a vessel 33, with its distal end located immediately adjacent to an occlusion 35. In this case, the occlusion is only partial, with a narrow opening 37 located near the vessel's centerline. In addition to the sheath 25 and optical fiber 27, the assembly further includes a mechanical device such as an inflatable balloon or bladder 39 for use in centering the assembly within a healthy part of the vessel. The assembly is moved axially through the vessel to its desired location, after which the bladder is inflated by pressurizing it with saline solution, or radio opaque contrast media, provided through one of the tubes 31a or 31b connected to the assembly via the input device 29. The entire procedure may be easily monitored by conventional x-ray fluoroscopy.

An elongated fiber guide or holder 41 is positioned within the tubular sheath 25, for supporting the optical fiber 27. In particular, a cylindrical channel is formed along the guide's entire length, the channel being of a size to slidably receive the optical fiber. The fiber guide has an outside diameter approximately the same as the inside diameter of the sheath, at least in the region of the assembly's distal end. The abutting surfaces of the fiber guide and the sheath are of high lubricity, to facilitate a convenient rotation with minimum torque of the fiber guide about its longitudinal axis. As shown in FIG. 1, a conventional stepper motor 43 controllably rotates the fiber guide through a collar 45 secured to the holder at its proximal end.

With particular reference now to FIGS. 2–5, it will be observed that the channel in the fiber guide 41 that slidably receives the optical fiber 27 is angularly skewed at its distal end relative to the guide's centerline. The channel emerges from the guide's distal end at a point substantially coincident with the guide's centerline. Thus, when the optical fiber's distal tip is coterminous with the fiber guide's distal end (FIG. 2), the laser beam being transmitted along the fiber will be emitted at a point at or very near the vessel's centerline.

As previously mentioned, the optical fiber 27 is selectively slidable along the channel formed in the fiber guide 41. When the fiber has been slid axially forwardly to the location depicted in FIG. 4, the catheter assembly 21 will emit the laser beam at a point radially spaced from the vessel's centerline. Consequently, in this configuration, the catheter assembly can be used to remove a section of the occlusion 35 located radially outwardly from the vessel's centerline. Rotating the fiber guide 41 relative to the sheath 25 using the motor 43 and collar 45 will cause the exposed distal end of the optical fiber to sweep in a conical motion, whereby a ring-shaped section of the occlusion, concentric with the vessel's centerline, can be removed.

The rotation rate of the fiber guide 41 is preferably less than about 1000 rpm, and the pulse repetition rate of the laser 23 (FIG. 1) is preferably synchronized with the rotation rate, so that successive laser pulses do not spatially overlap on the beam's circumferential path. This reduces any thermal build-up and minimizes damage in the surrounding tissues. Alternatively, the fiber guide 41 may be rotated manually. Such manual rotation is particularly effective when removing an obstruction from a vessel in an intraoperative procedure, in which the catheter assembly is very short and inserted into the vessel through an incision located near the obstruction.

Figure 5:
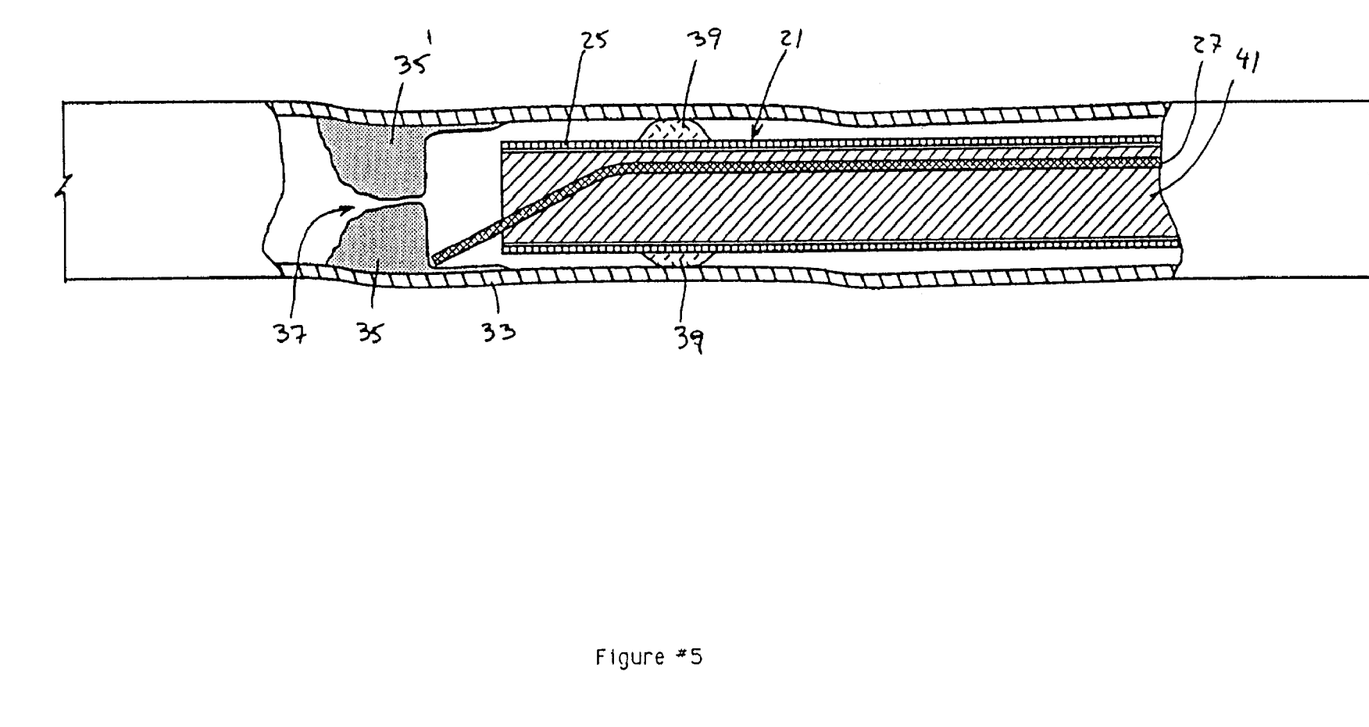
FIG. 5 is a side, cross-sectional view similar to FIG. 4, but with the optical fiber extended even further, to a position where its distal tip lies radially beyond the catheter outer wall, allowing a hole to be created that is larger than the catheter diameter.

It will be appreciated that by incrementally advancing the optical fiber 27 axially through the channel in the fiber guide 41, a series of rings of progressively larger radius can be removed from the occlusion 35. At its extreme, the optical fiber can even be moved axially forwardly through the fiber holder to a point where its distal tip projects radially beyond the sheath 25. This enables the removal of a ring-shaped section of the occlusion larger even than the sheath. Such a position for the optical fiber is depicted in FIG. 5.

Rotating the fiber holder 41 about its longitudinal axis causes relative motion between the optical fiber 27 and the holder and between the holder and the sheath 25. The optical fiber and the sheath both remain rotationally stationary, although, as described above, the skewing of the fiber holder's channel causes the fiber's angular orientation to vary with the rotation.

Significantly, the lack of relative motion between the catheter assembly's sheath 25 and the wall of the vessel 33 avoids the possibility of the vessel wall tissue being mechanically damaged. In the absence of the sheath, rotation of the fiber holder could otherwise rub the vessel wall so as to injure endothelial cells and thereby trigger a hyperplastic response, which could lead to restinosis in the vessel. The sheath effectively isolates the rotating fiber holder from the vessel wall and thus obviates this problem.

After the catheter assembly 21 has been used to remove a central segment and a series of contiguous ring-shaped segments, as described above, the assembly can be advanced incrementally forwardly within the vessel 33 and the process repeated to remove an additional layer of contiguous ring-shaped segments from the occlusion. This sequential process can be repeated until the occlusion has been completely removed, or at least removed sufficiently to enable adequate blood flow through the vessel. The assembly is preferably used in treating vessels having occlusions that occur in relatively non-tortuous regions and that have lengths of a few centimeters or less. Otherwise, difficultly might be encountered in maintaining the assembly's distal end properly centered within the vessel. In order to treat very tortuous vessels, it would most likely be necessary to augment the catheter apparatus with an additional form of guidance and visualization, such as that provided by angioscopy or intravascular ultra-sound. Ideally, the inflatable bladder 39 for use in centering the assembly's distal end always engages portions of the vessel wall that are proximal to the occlusion and proximal to those portions of the occlusions removed during the initial stages of its removal.

Figure 6:
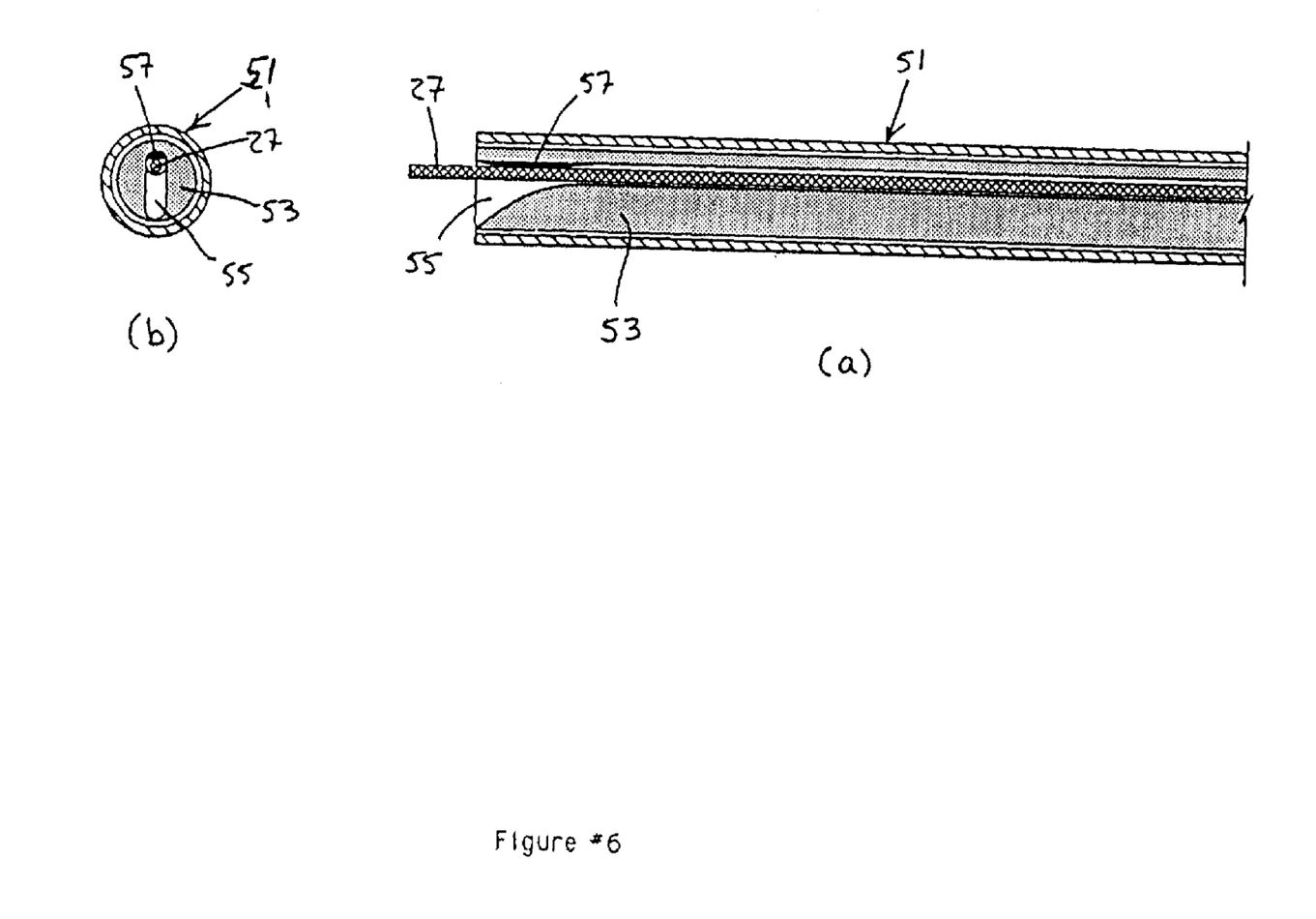
FIG. 6a and FIG. 6b are a side, cross-sectional view and an end view, respectively, of the distal end of a second embodiment of a catheter assembly in accordance with the invention, shown with a positioning bladder deflated and the optical fiber positioned at one extreme of its range of lateral motion.

With reference now to FIGS. 6(a) and (b) and FIGS. 7(a) and (b), there is shown the distal end of a second preferred embodiment of a catheter assembly 51 in accordance with the invention. This second embodiment is similar to the first embodiment of FIGS. 2–5, except that the distal end of its fiber guide 53 supports the optical fiber 27 in a slot 55 having a non-circular cross-section. The slot is sized in the circumferential direction to be substantially the same as the optical fiber's diameter, but is sized in the radial direction to be much wider. This permits the fiber's distal end to be moved radially, thereby facilitating the use of the catheter assembly to sculpt out large portions of occlusions formed in the vessel.

Figure 7:
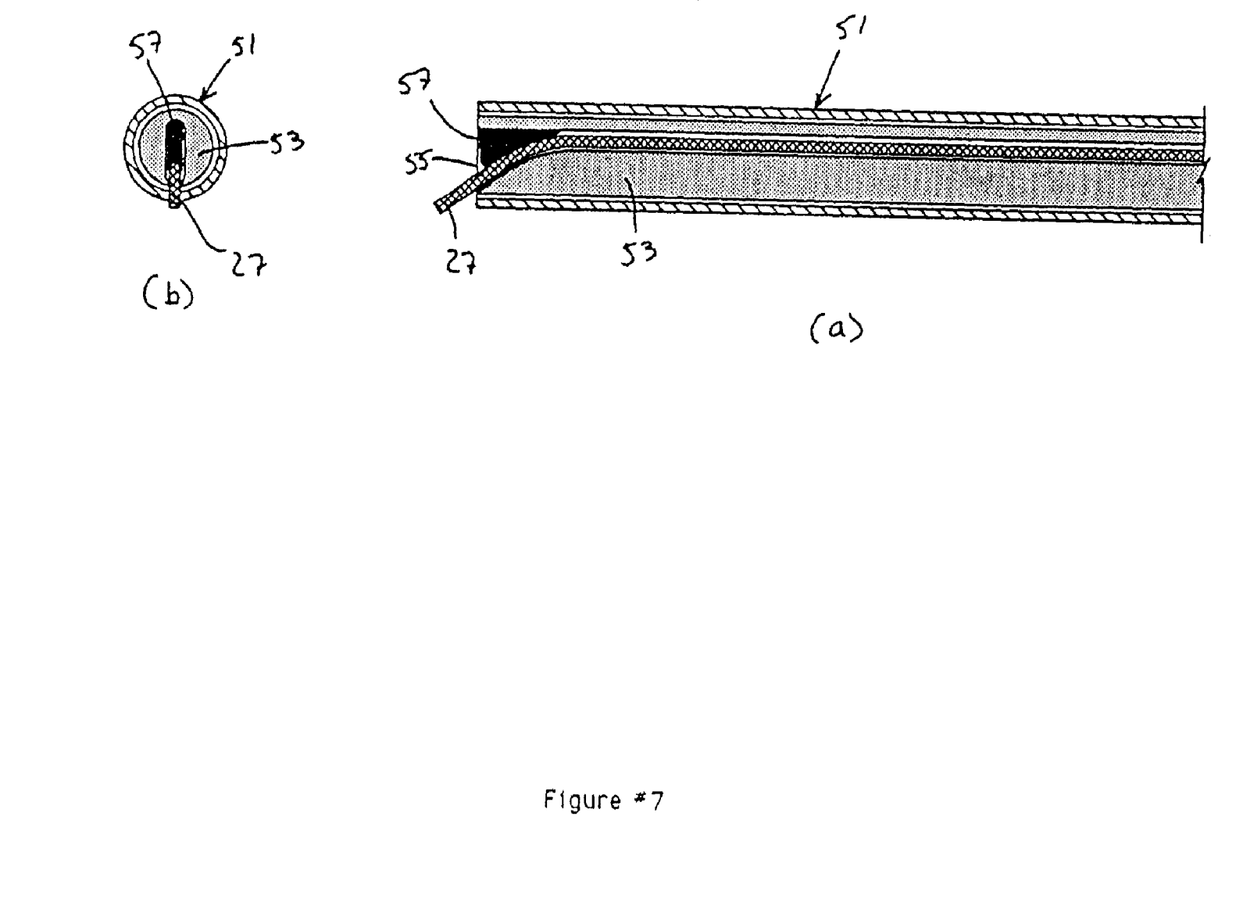
FIG. 7a and FIG. 7b are views similar to FIG. 6a and FIG. 6b, respectively, but with the bladder pressurized and the optical fiber urged to the opposite extreme of its range of lateral motion.

To controllably move the optical fiber's distal tip radially within the slot 55, this second embodiment 51 further includes an inflatable bladder 57 positioned within the fiber guide 53 so as to apply a lateral pressure to the fiber 27. The bladder is controllably inflated using a pressurized saline solution delivered to it via one of the tubes associated with the assembly's input device 29 (FIG. 1). FIGS. 6(a) and 6(b)

show the bladder in its fully deflated condition, such that the fiber's distal end remains centrally located within the fiber holder 53. FIGS. 7(*a*) and 7(*b*), show the bladder fully inflated such that the fiber's distal end is urged radially outwardly to its furthest outward position. The bladder may be inflated in either a continuous fashion or a step-wise fashion.

This second catheter assembly embodiment 51 is used in much the same fashion as the embodiment 21 of FIGS. 2–5, the only significant difference being in the manner in which the optical fiber's distal end is moved incrementally in the radial direction. Rather that moving the fiber 27 axially forwardly to increase the radial position of its distal tip, the bladder is incrementally inflated. In each incremental position, either a central segment or a ring-shaped segment is removed from the occlusion 35. After an entire layer of contiguous ring-shaped sections have been removed, the catheter assembly is moved incrementally forwardly within the vessel 33, to facilitate the removal of a succeeding layer. It will be noted that the axial position of the fiber's distal tip remains substantially the same for all of its successive radial positions. This ensures that each successive layer of contiguous, ring-shaped sections that is removed from the occlusions is substantially planar.

Figure 8:
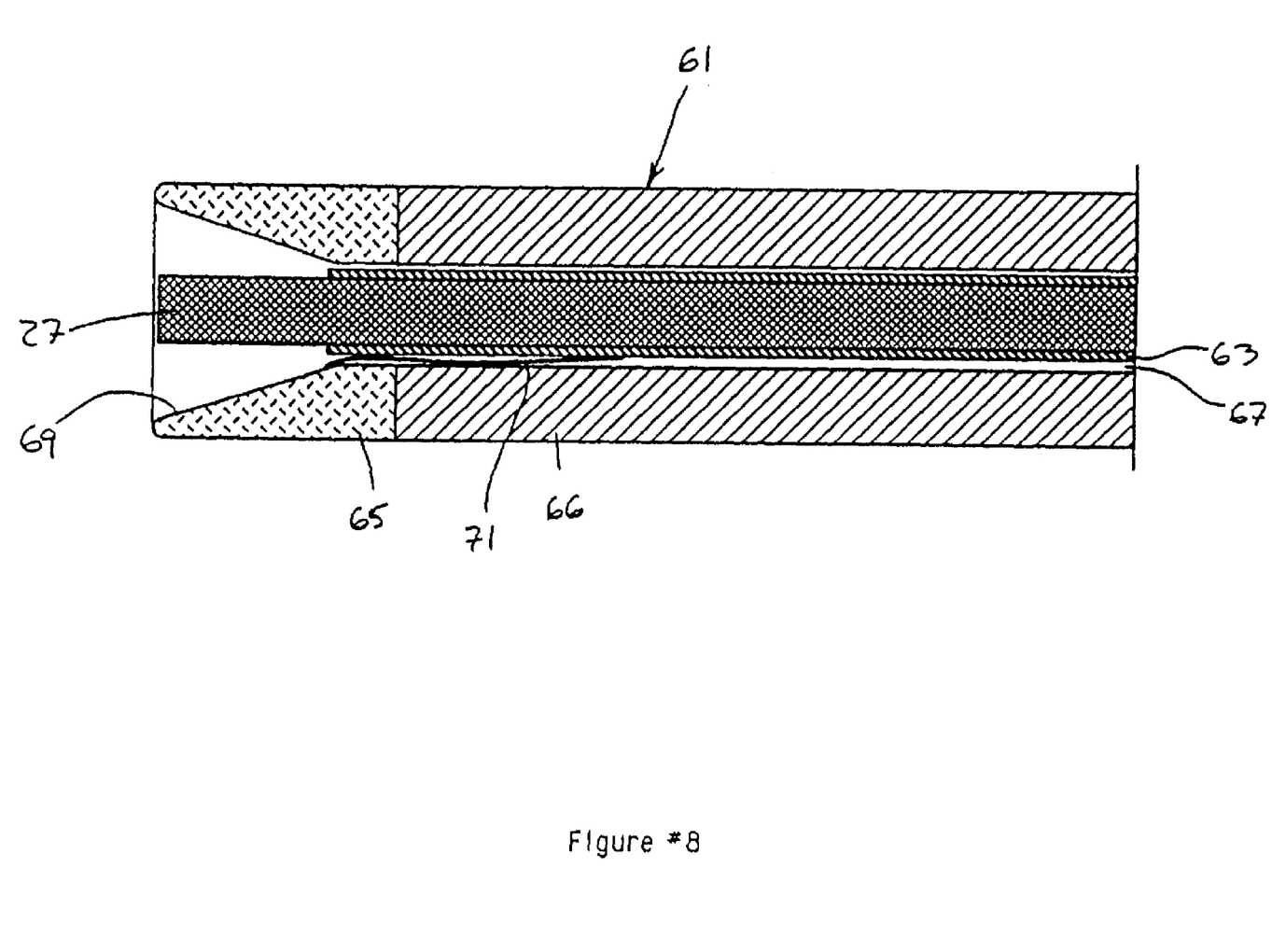
FIG. 8 is a side, cross-sectional view of a third embodiment of a catheter assembly in accordance with the invention, shown with the optical fiber retracted such that its distal tip is located centrally within a fiber holder of the assembly.
Figure 9:
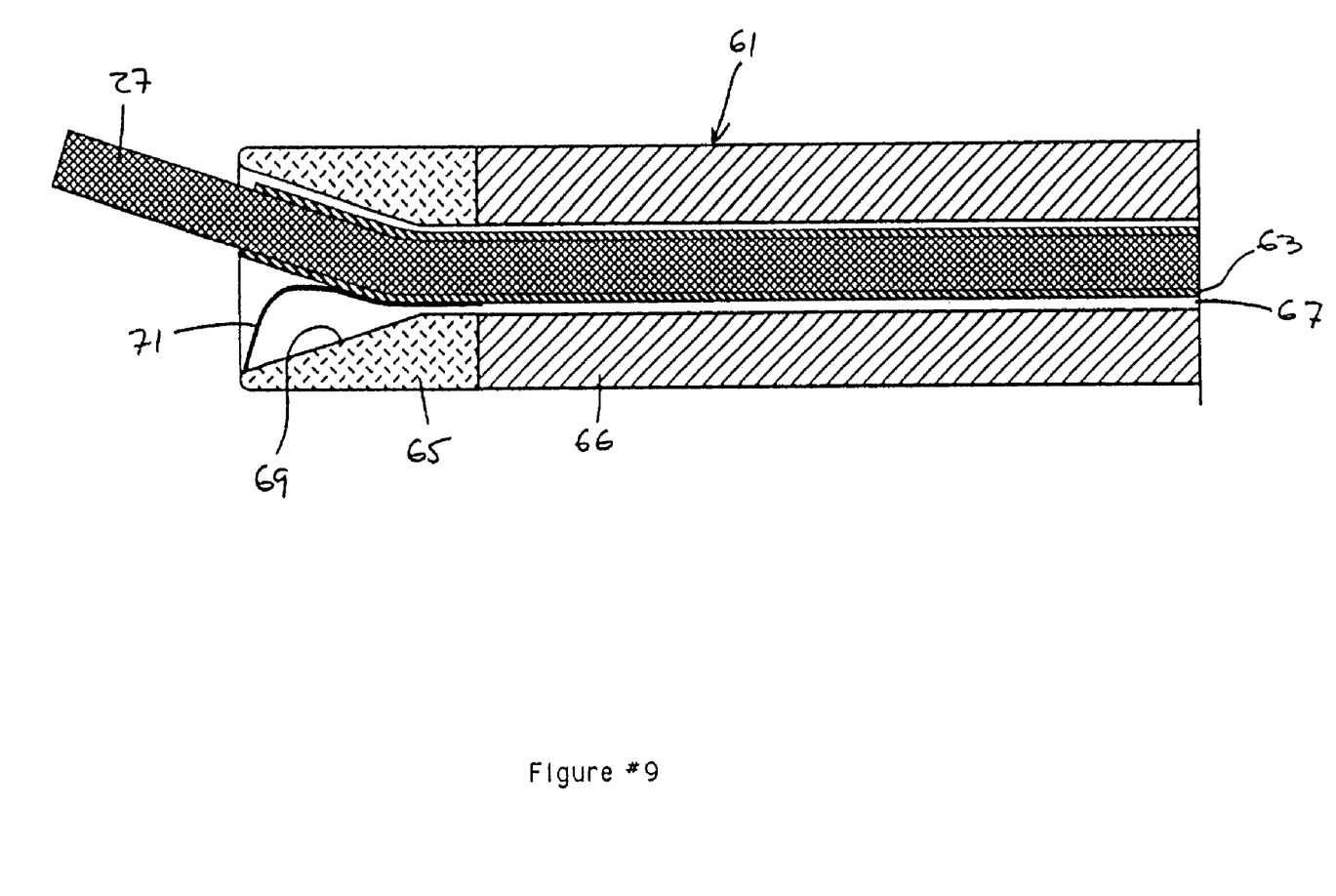
FIG. 9 is a side, cross-sectional view of the distal end of the catheter assembly of FIG. 8, but with the optical fiber axially extended such that its distal tip is urged laterally by a leaf spring biased against a flared opening in the fiber holder.

FIGS. 8 and 9 depict the distal end of a third catheter assembly embodiment 61 in accordance with the invention. In this embodiment, an elongated fiber guide 63 terminates within a body 65 at the distal end of the assembly's sheath 66. The body and sheath include a central passageway 67 of circular cross-section, for receiving the fiber guide and allowing the fiber guide to rotate relative to it, about its longitudinal axis. The distal end of the passageway flares outwardly to define a generally conical surface 69 in the body.

Attached to the exterior surface of the fiber guide, near its distal end, is a leaf spring 71. When the fiber guide is axially positioned with the leaf spring located within the passageway 67 of the body 65 and sheath 66, the leaf spring is forced to a straight position, parallel with the fiber guide's longitudinal axis. As the fiber guide 63 and optical fiber 27 are moved axially forwardly to bring a portion of the spring into the region of the conical surface 69, however, the spring and fiber are yieldably urged apart from each other, so as to position the fiber's distal tip at a radial location spaced from the centerline of the body and vessel. Eventually, continued forward axial movement of the fiber will cause the fiber's distal tip to be moved to the maximum deflected angle. The optical fiber can be moved axially within the spring-deflected guide, to control the radial position of the fiber's distal tip relative to the assembly's centerline.

As with the first two embodiments, this third catheter assembly embodiment 61 is used to sequentially remove first a center section and then a series of contiguous ring-shaped sections from the occlusion. After a single layer of such sections has been removed, the catheter assembly is advanced forwardly within the vessel to facilitate the removal of a second and subsequent layers. As with the first two embodiments, this third catheter assembly embodiment also can be used to remove ring-shaped sections from the occlusion having a radius greater than that of the assembly's sheath.

Figure 10:
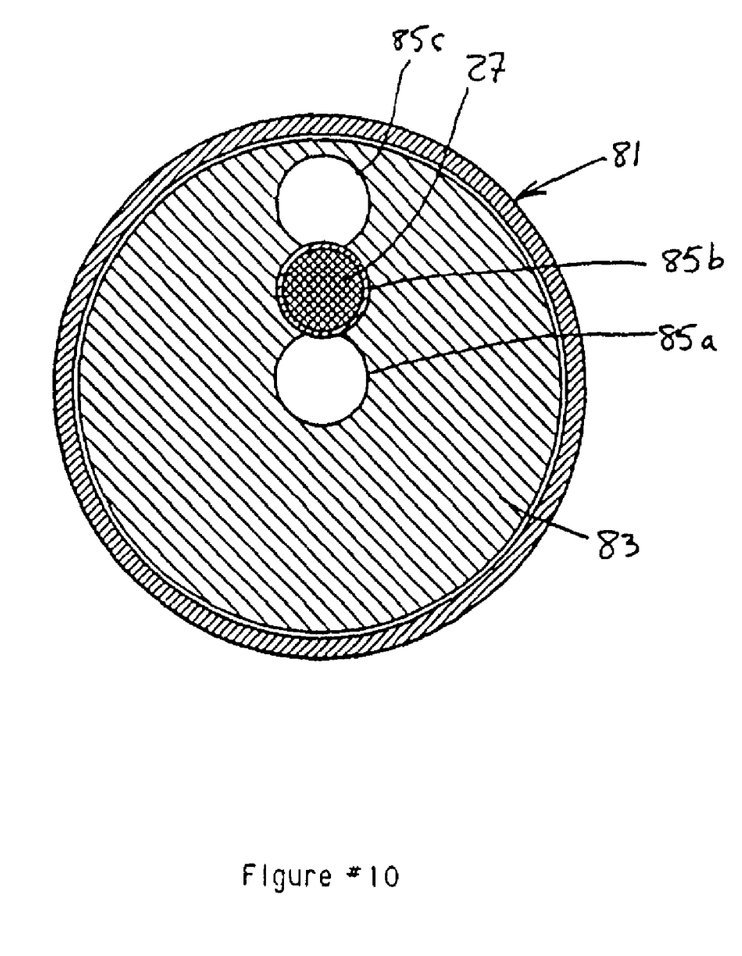
FIG. 10 is an end view of a fourth embodiment of a catheter assembly in accordance with the invention, showing three channels sized to receive the optical fiber and position its distal tip at a three selected radii.

FIG. 10 is an end view of the distal end of a fourth catheter assembly embodiment 81 in accordance with the invention. This embodiment includes a fiber holder 83 having a set of three separate channels 85*a*, 85*b* and 85*c* for slidably receiving the optical fiber 27. Each such channel is located at a different radial position within the fiber holder. The catheter assembly is used by placing the optical fiber sequentially in each of the separate channels, each time the assembly being used to sculpt out of the occlusion either a central section or a concentric ring-shaped section. The separate channels are sized and positioned such that the successive sections are all contiguous with each other. Some overlap is required to compensate for the presence of cladding on the optical fiber's outer surface.

Figure 11:
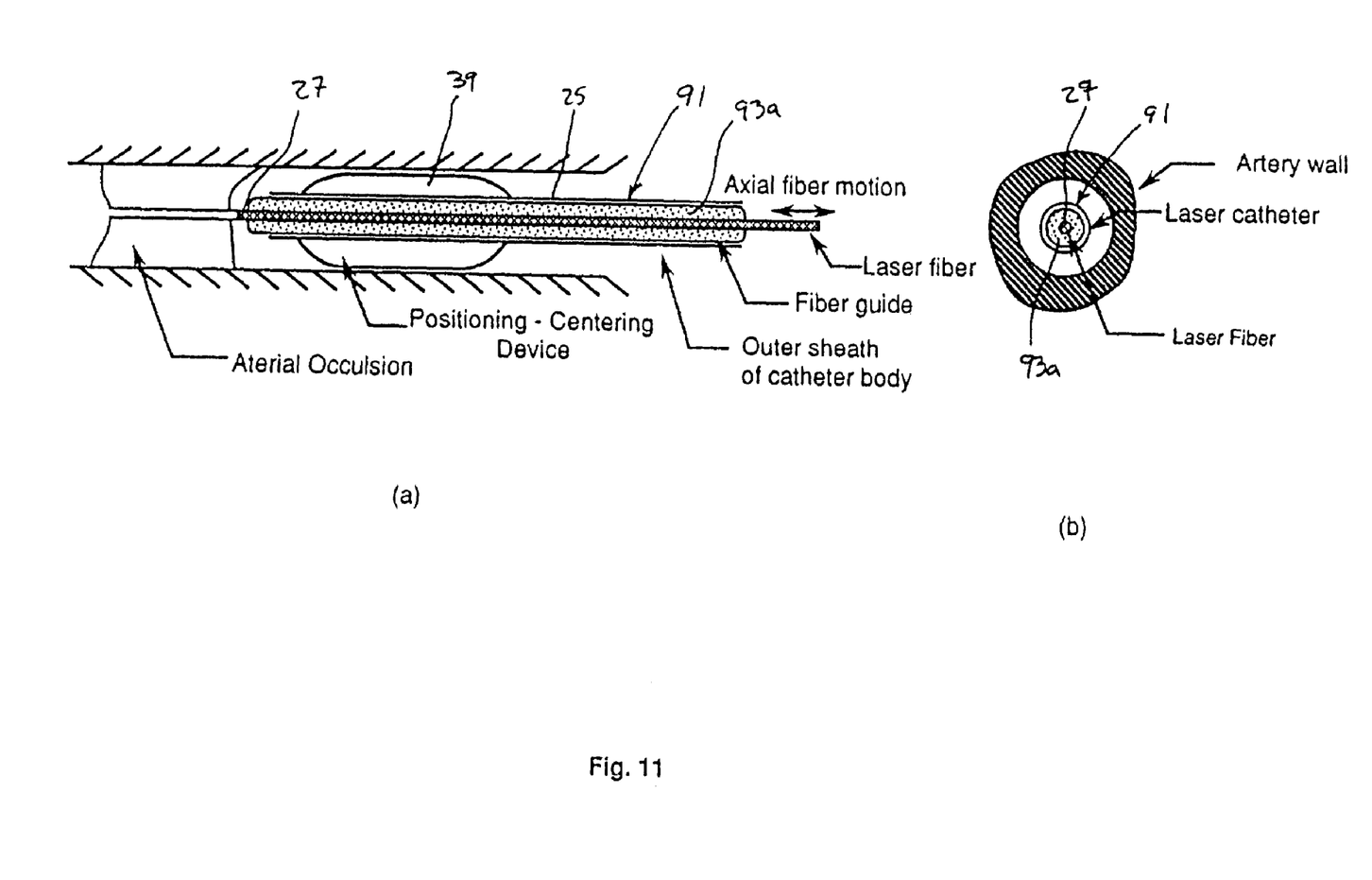
FIG. 11a and FIG. 11b are a side, cross-sectional view and an end view, respectively, of the distal end of a fifth embodiment of a catheter assembly in accordance with the invention, showing one of several optical fiber guides used sequentially, the depicted guide positioning the fiber's distal tip centrally within the assembly.
Figure 12:
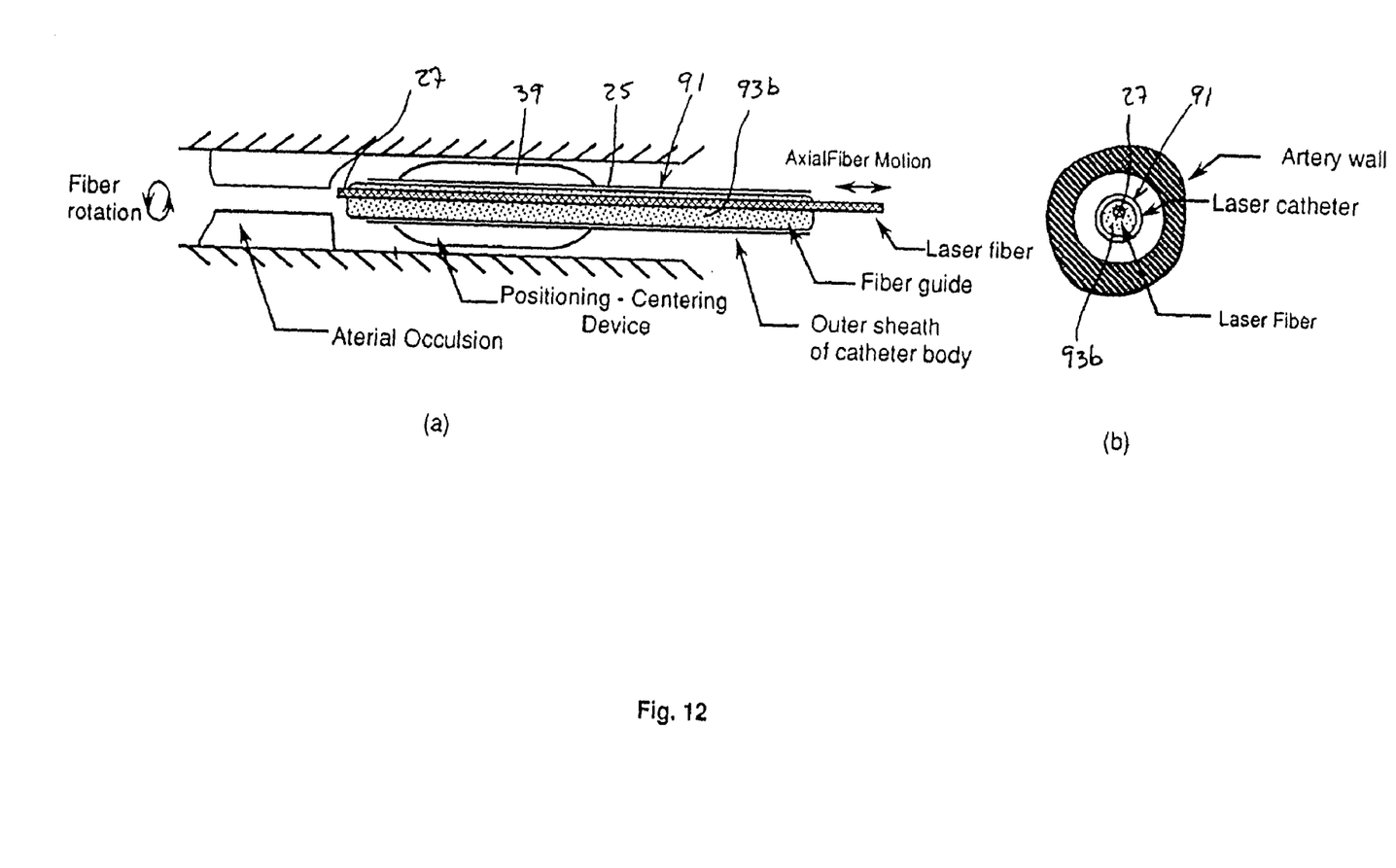
FIG. 12a and FIG. 12b are views similar to FIG. 11a and FIG. 11b, respectively, but showing a second optical fiber holder, this holder positioning the fiber's distal tip at an intermediate radial position.
Figure 13:
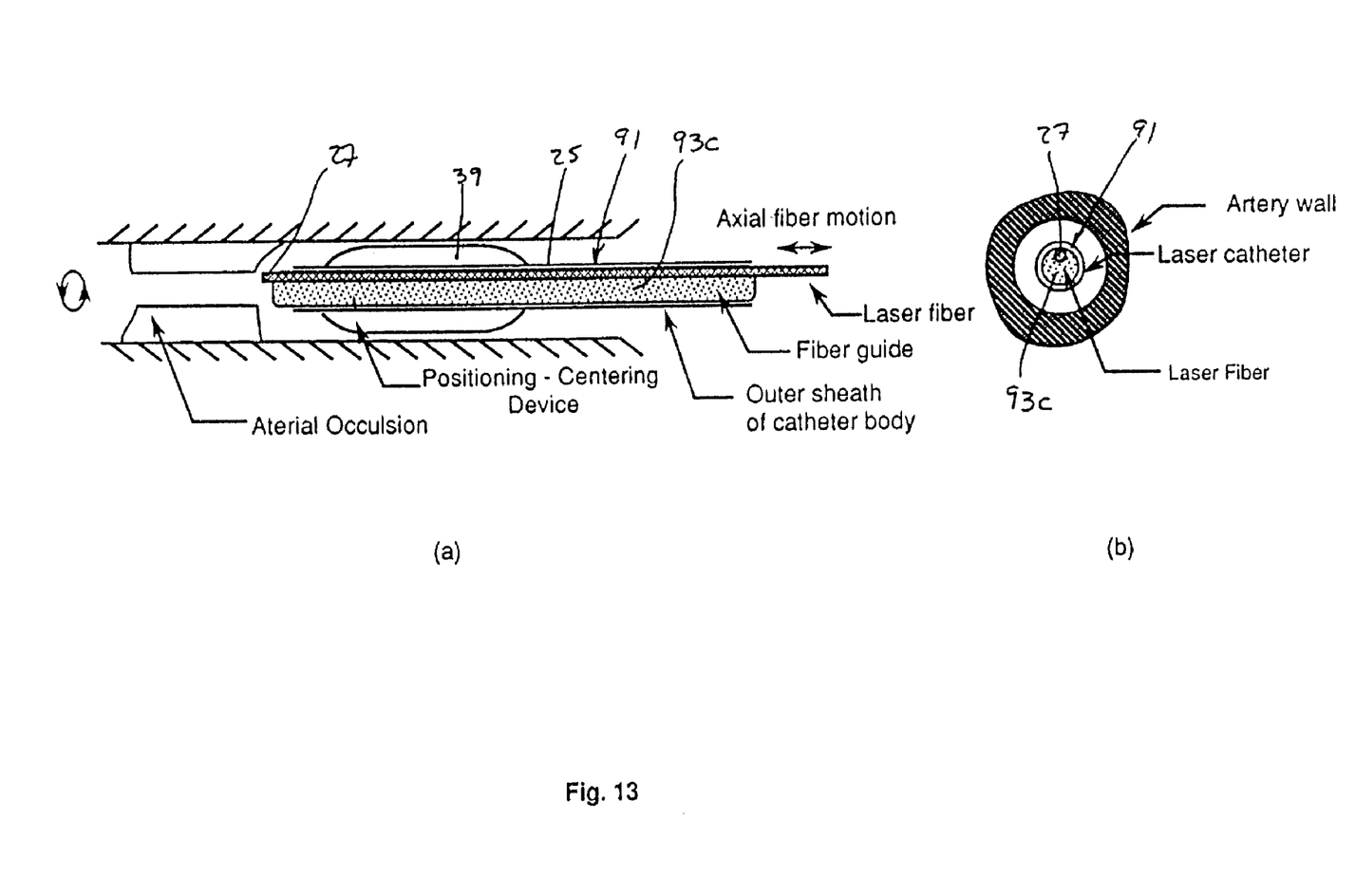
FIG. 13a and FIG. 13b are views similar to FIG. 11a and FIG. 11b, respectively, but showing a third optical fiber holder, this holder positioning the fiber's distal tip at a maximum radial position.

FIGS. 11–13 depict a fifth catheter assembly embodiment 91 in accordance with the invention. In this embodiment, three separate fiber guides 93*a*, 93*b* and 93*c* are utilized in sequence. Each guide supports the optical fiber 27 at a different radial position. The guide 93*a* (FIGS. 11(*a*) and 11(*b*)) supports the fiber in a central position, the guide 93*b* (FIGS. 12(*a*) and 12(*b*)) supports the fiber at an intermediate radial position, and the guide 93*c* (FIGS. 13(*a*) and 13(*b*)) supports the fiber at an extreme radial position.

Initially, the fiber guide 93*a* is used such that the catheter assembly 91 removes a central section, approximately the diameter of the fiber 25, from the occlusion in the vessel. With this fiber guide 93*a* in position, the fiber, itself, can be moved axially forwardly through the guide so as to remove a succession of centrally-located sections from the occlusion. Next, the fiber guide 93*b* is substituted for the guide 93*a* and a ring-shaped section, concentric with the initially-removed section, is removed. Again, the optical fiber can be moved incrementally forwardly through the guide 93*b* to remove a succession of ring-shaped sections from the occlusion. Finally, the fiber guide 93*c* is substituted for the guide 93*b* and the process repeated for a succession of further ring-shaped sections.

It should be appreciated from the foregoing description that the present invention provides an improved fiber optic laser catheter assembly for use in removing, or largely debulking, obstructions or occlusions from a lumen in a living body. In all of the disclosed embodiments, the obstructions are removed by controllably positioning an optical fiber's distal tip in a succession of selected radial and circumferential positions so as to sculpt away the obstruction without substantial risk of mechanically or thermally damaging the vessel. Several of the embodiments are configured such that the portion of the occlusion that can be reliably sculpted away has a radius greater even than the radius of the catheter assembly itself.

Although the invention has been described in detail with reference to the presently preferred embodiments, those of ordinary skill in the art will appreciate that various modifications can be made without departing from the invention. Accordingly, the invention is defined only by the following claims.

What is claimed is:

1. A method for removing an obstruction from a lumen of a living body, the method comprising:

providing a catheter including a tubular outer sheath sized to be received within the lumen of the living body, the sheath including a longitudinal axis and a distal end, and an optical fiber line extending through the sheath, the optical fiber line disposed in an optical fiber guide located within the sheath;

arranging the distal end of the sheath to be located proximal to the obstruction;

generating a pulsed laser beam using a laser, the pulsed laser beam comprising laser pulses having a repetition rate, the optical fiber line in the sheath including an inlet end that receives the pulsed laser beam and an outlet end located proximal to the obstruction, the optical fiber guide configured to support at least the outlet end of the optical fiber line;

displacing the outlet end of the optical fiber line a radial distance from the longitudinal axis of the sheath;

rotating the fiber guide about the longitudinal axis of the sheath so that the outlet end of the optical fiber line follows a circumferential pathway within the lumen;

adjusting the rotation rate of the fiber guide based on the pulse repetition rate of the pulsed laser beam so that successive laser pulses do not substantially spatially overlap on the circumferential pathway of the outlet end of the optical fiber line; and varying the radial distance of the outlet end of the optical fiber line from the longitudinal axis of the sheath.

2. The method of claim 1, wherein the step of varying the radial distance includes controllably inflating a bladder to laterally bias a distal tip of the optical fiber line within a radially-aligned slot formed in the optical fiber guide.

3. The method of claim 1, wherein the bladder is configured to expand and to compressively engage the optical fiber guide towards a portion of a wall of the lumen proximal to the obstruction to be removed.

4. The method of claim 1, wherein the step of varying the radial distance includes placing the optical fiber line in at least one of a plurality of channels formed in the optical fiber guide, each channel including a distal end located at a different radial position.

5. The method of claim 1, wherein the step of varying the radial distance includes placing the optical fiber line in at least one of a plurality of separate optical fiber guides, each guide including a distal end located at a different radial position.

* * * * *